US009295252B2

(12) United States Patent
Probasco et al.

(10) Patent No.: US 9,295,252 B2
(45) Date of Patent: Mar. 29, 2016

(54) COMPOSITIONS AND METHODS FOR CONTROLLING A TROPILAELAPS PARASITIC MITE

(71) Applicant: John I. Haas, Inc., Washington, DC (US)

(72) Inventors: Gene Probasco, Yakima, WA (US); Fabiana Ahumada, Tucson, AZ (US); Lloyd Schantz, Washington, DC (US)

(73) Assignee: John I. Haas, Inc., Washington, DC (US)

( * ) Notice: Subject to any disclaimer, the term of this patent is extended or adjusted under 35 U.S.C. 154(b) by 0 days.

(21) Appl. No.: 14/406,150

(22) PCT Filed: Jun. 7, 2013

(86) PCT No.: PCT/US2013/044757
§ 371 (c)(1),
(2) Date: Dec. 5, 2014

(87) PCT Pub. No.: WO2013/185059
PCT Pub. Date: Dec. 12, 2013

(65) Prior Publication Data
US 2015/0150252 A1    Jun. 4, 2015

Related U.S. Application Data

(60) Provisional application No. 61/656,629, filed on Jun. 7, 2012.

(51) Int. Cl.
*A01N 65/00* (2009.01)
*A01N 35/06* (2006.01)
*A61K 36/185* (2006.01)
*A01K 47/06* (2006.01)
*A01N 25/08* (2006.01)

(52) U.S. Cl.
CPC ............... *A01N 35/06* (2013.01); *A01K 47/06* (2013.01); *A01N 25/08* (2013.01); *A61K 36/185* (2013.01)

(58) Field of Classification Search
CPC ........................................................ A61K 36/00
USPC .......................................................... 424/725
See application file for complete search history.

(56) References Cited

U.S. PATENT DOCUMENTS

| 4,876,265 A | 10/1989 | Schmid |
| 2001/0014346 A1 | 8/2001 | Watkins |
| 2002/0051804 A1 | 5/2002 | Probasco et al. |
| 2007/0232188 A1 | 10/2007 | Probasco |
| 2007/0248549 A1 | 10/2007 | Kuhrts |

FOREIGN PATENT DOCUMENTS

| WO | 2008/060591 A2 | 5/2008 |
| WO | 2009/098300 A2 | 8/2009 |
| WO | 2009/099646 A1 | 8/2009 |

OTHER PUBLICATIONS

International Search Report of PCT/US2013/044757 dated Dec. 12, 2013.
Jones, G., et al.; "Repellent and Oviposition-Deterring Effects of Hop Beta-Acids on the Two-Spotted Spider Mite Tetranychus Urticae"; Pesticide Science, 1996, Vo. 47, pp. 165-169.
Degrandi-Hoffman, G., et al.; "The Effects of Beta Acids From Hops (Humulus lupulus) on Mortality of Varroa Destructo (Acari: Varroidae)"; Experimental and Applied Acarology, Jul. 6, 2012, vol. 58, pp. 407-421.
Extended European Search Report mailed Oct. 20, 2015 in connection with EP13800867.7.
[No Author Listed] Chapter 2.2.6: Tropilaelaps infestation of honey bees (*Tropilaelaps* spp.). OIE Terrestrial Manual 2008:419-423. Retrieved from the Internet: http://www.oie.int/fileadmin/Home/eng/Health_standards/tahm/2.02.06_TROPILAELAPS.pdf last accessed Jan. 6, 2016.
Sharma et al., Efficacy of some acaricides against extoparasitic mite *Tropilaelaps clareae* infesting European honey bee *Apis mellifera*. Indian J Agric Res. Mar. 1, 2003:37(1):60-3.

*Primary Examiner* — Michael Meller
(74) *Attorney, Agent, or Firm* — Wolf, Greenfield & Sacks, P.C.

(57) ABSTRACT

As described below, the present invention provides methods and compositions for controlling the honey bee parasitic mite *Tropilaelaps*. In addition, the invention features compositions useful for the treatment or prevention of a *Tropilaelaps* parasitic mite infestation in a honey bee hive.

4 Claims, 1 Drawing Sheet

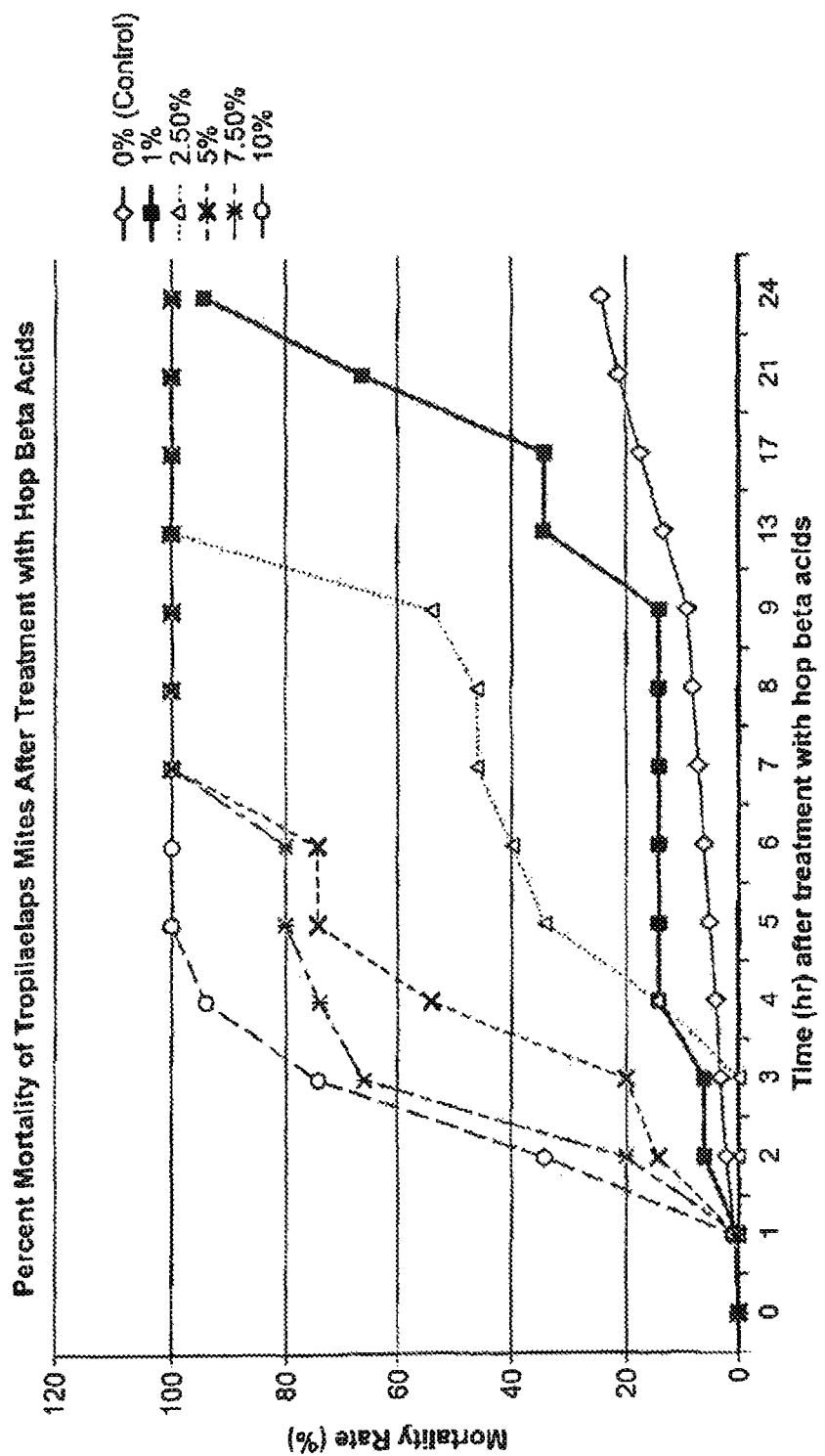

COMPOSITIONS AND METHODS FOR CONTROLLING A TROPILAELAPS PARASITIC MITE

CROSS-REFERENCE TO RELATED APPLICATIONS

This application is the national phase under 35 U.S.C. §371 of PCT International Application No. PCT/US2013/044757, filed Jun. 7, 2013, which claims the benefit of U.S. Provisional Patent Application Serial No. 61/656,629, filed Jun. 7, 2012. The entire contents of each applications are hereby incorporated by reference herein.

BACKGROUND OF THE INVENTION

Honey bees, *Apis mellifera*, are required for the effective pollination of crops and are therefore critical to world agriculture. Honey bees also produce economically important products, including honey and bees wax. Honey bees are susceptible to a number of parasites and pathogens, including the ectoparasitic mite, *Varroa destructor*, which is presently wrecking havoc on honey bee colonies throughout the United States, Europe, and many other countries. On the horizon is a new threat to honey bee colonies. *Tropilaelaps clareae, Tropilaelaps koenigerum, Tropilaelaps mercedesae*, and *Tropilaelaps thaii* (collectively, "*Tropilaelaps*") (Acari: Laelapidae) are Asian mites that affect developing brood and adult honey bees. Infestation by *Tropilaelaps* can cause abnormal brood development and the death of brood and adult bees. The natural host of *Tropilaelaps* is the giant Asian honey bee, *Apis dorsata*, but *Tropilaelaps* can readily infest colonies of *Apis mellifera*, the Western honey bee and Asian honey bees, such as *Apis laboriosa, Apis cerana* and *Apis florea*.

Maintaining a supply of strong honey bee colonies available for pollination is essential for the sustained production of farm crops. Many honey bee colonies have already been weakened due to *Varroa* infestation. Introduction of *Tropilaelaps* into these already weakened populations could cause the wide-spread collapse of honey bee colonies. Current methods of treating *Varroa* and *Tropilaelaps* infestations are proving to be ineffective. In addition, the use of such miticides may introduce injurious chemicals into honey that is intended for human consumption. New compositions and methods for treating or preventing mite infestations are urgently required. Desirably, such compositions would include only natural ingredients that pose no risk to human health.

SUMMARY OF THE INVENTION

As described below, the present invention features methods and compositions for reducing a *Tropilaelaps* infestation in a honey bee hive.

In particular embodiments, the invention provides a strip comprising a liquid composition comprising at least about 0.1%-20% (e.g., 0.1, 0.5, 1.0, 2, 4, 5, 6, 7, 8, 9, 10, 15, 20%) potassium salts of hop beta acids or at least about 30-35% beta acid resins in solvent (e.g. propylene glycol), and an emulsifier (e.g., polysorbate). Preferably the strips are moistened with a solution or emulsion comprising equal parts beta acid resins, propylene glycol, and polysorbate 60. In one embodiment, the beta acid resins comprise about 10-20% potassium salts of hop beta acids (e.g., 10, 11, 12, 13, 14, 15, 16, 17, 18, 19, 20%). In one preferred embodiment, the strips comprise a liquid composition comprising about 16% potassium salts of hop beta acids.

Other features and advantages of the invention will be apparent from the detailed description, and from the claims.

DEFINITIONS

By "acarid" is meant an arachnid of the order Acarina, which includes mites and ticks. Exemplary acarids include *Tropilaelaps clareae, Tropilaelaps koenigerum, Tropilaelaps Mertcedesae*, and *Tropilaelaps thaii*.

By "alpha acid" is meant an organic acid derived from a hop plant (*Humulus lupulus*) having structural homology to a humulone, adhumulone, cohumulone, or an analog or derivative thereof. Humulone, adhumulone, and cohumulone are the three most abundant alpha acid analogs. Other exemplary derivatives of an alpha acid include, but are not limited to isoalpha acids, rhoisoalpha acids, tetrahydroisoalpha acids, and hexahydroisoalpha acids.

By "beta acid" is meant an organic acid derived from a hop plant (*Humulus lupulus*) having structural homology to a lupulone, adlupulone, colupulone or an analog or derivative thereof. Lupulone, adlupulone, and colupulone are the three most abundant beta acid analogs. Other exemplary derivatives of a beta acid include, but are not limited to, hulupones, hexahydrobeta acids and hexahydro hulupones.

By "biological function" is meant any physiological or behavioral activity of an organism. Exemplary biological functions include reproduction, respiration, neural activity, locomotion. Honey production is a biological function that is specific to a honey bee.

In this disclosure. "comprises," "comprising," "containing" and "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

By "contacting" is meant touching, associating with, or having proximity to a composition. For example, a hop derivative may contact a hive either inside or outside of the hive structure.

By "controlled release" is meant released over the course of hours, days, weeks, or months.

By "controlling a parasitic mite" is meant inhibiting mite survival or reducing, slowing, or stabilizing the growth of a mite population. In one embodiment, the invention reduces *Tropilaelaps clareane, Tropilaelaps koenigerum, Tropilaelaps mercedesae*, and *Tropilaelaps thaii* infestation of a honey bee, honey bee colony, or hive (e.g., box hive). In another embodiment, the invention reduces *Tropilaelaps clareae* and *Tropilaelaps koenigerum* infestation of a honey bee, honey bee colony, or hive (e.g., box hive). In other embodiments, a composition of the invention kills or repels the parasitic mite.

By "comb" is meant sections of hexagonal bee wax cells that are used to rear honey bee progeny ("brood") and store honey and pollen.

By "effective amount of a miticide" is meant an amount effective to disrupt a mite biological function.

By "emulsion" is meant a mixture comprising at least two immiscible liquids. Typically, one of the liquid is dispersed in small droplets in the second liquid. Preferably, the emulsion is a stable emulsion where the two phases remain stably mixed for hours, days, or weeks. The emulsion may or may not contain an added emulsifier.

By "hive" is meant a man-made structure that contains a bee colony. A modern box hive typically includes a bottom board, cover, and one or more boxes, stacked one above the other. Inside, each box contains a series of movable frames of comb or foundation held in a vertical position a bee space apart.

By "honey bee" is meant a Hymenopteran insect of the genus *Apis*. The term "honey bee" is not limited to the adult form of the insect, but encompasses all honey bee developmental stages, including but not limited to egg, larva, and pupa. Exemplary honey bee species include *Apis andreniformis*, *Apis cerana*, *Apis dorsata*, *Apis florea*, *Apis koschevnikovi*, *Apis laboriosa* and *Apis mellifera*.

By "honey bee colony" is meant a community of bees. Honey bee colonies may occur in the wild or may be maintained by bee keepers.

By "honey bee parasitic mite" is meant any acarid that parasitizes a honey bee or infests a honey bee hive. In particular embodiments, the mite is a member of the Family Varroidae, Family Laelapidae, or Family Tarsonemidae. Exemplary honey bee parasitic mites include *Acarapis woodi*. *Acarapis dorsalis*, *Acarapis externus*, Euvarroa sinhai, Euvarroa wongsirii, Tropilaelaps mites (e.g., *Tropilaelaps clareae*, *Tropilaelaps koenigerum*, *Tropilaelaps mercedesae*, and *Tropilaelaps thaii*), *Proctolaelaps regalis*, *Varroa* mites (e.g., *Varroa jacobsonii*, *Varroa rinderer*), and tracheal mites.

By "hop derivative" is meant any molecule that naturally occurs in hops (*Humulus lupulus*) and chemical derivatives thereof. Hop derivatives (e.g., alpha acids, beta acids) may be purified from hops or may be chemically synthesized.

By "infestation" is meant the colonization of a site or the parasitization of an organism by a pest.

By "isolated hop acid" is meant a hop acid of the invention that has been separated from one or more components that naturally accompany it in its native state. An isolated hop acid of the invention may be obtained, for example, by extraction from a natural source or by chemical synthesis. Purity can be measured by any appropriate method, for example, column chromatography, spectrophotometry, polyacrylamide gel electrophoresis, or by HPLC analysis.

By "miticide" is meant an agent that inhibits a biological function of a mite. Exemplary mites include *Tropilaelaps clarea*, *Tropilaelaps koenigerum*, *Tropilaelaps Mercedesae*, and *Tropilaelaps thaii*.

By "miticidal activity" is meant any activity that inhibits the growth, reproduction, or survival of a mite or other acarid. In one preferred embodiment, compositions of the invention reduce a *Tropilaelaps* infestation (e.g., *Tropilaelaps clareae*, *Tropilaelaps koenigerum*, *Tropilaelaps mercedesae*, and *Tropilaelaps thaii*) of a honey bee hive.

By "nucleus colony" is meant a package suitable for shipment comprising at least one queen, one or more bees, a honey frame, and a frame comprising brood. "Brood" refers to any one or more of egg, embryo, larva and pupal stages that develops within a bee hive. Typically, the nucleus colony is packaged in a box, crate, or other container suitable for shipment via courier or mail.

By "packaged bees" is meant a package suitable for shipment comprising at least one queen and one or more honey bees. Typically, packaged bees comprise a mated and/or laying queen and a number of bees (e.g., 1 lb, 2 lb, 3 lb, or more). The package is suitable for shipment via courier or mail.

By "preventing a mite infestation" is meant reducing the likelihood that a mite infestation will be established in an *Apis* colony.

By "treating a mite infestation" is meant reducing, stabilizing, or slowing the growth of a mite population in an *Apis* colony.

BRIEF DESCRIPTION OF THE DRAWINGS

FIG. 1 is a graph showing the percent mortality of *Tropilaelops* mites as a function of time after treatment with hop beta acids.

DETAILED DESCRIPTION OF THE INVENTION

The present invention is directed to methods and compositions to control *Tropilaelaps* spp., (e.g., *Tropilaelaps clareae*, *Tropilaelaps koenigerum*, *Tropilaelaps mercedesae*, and *Tropilaelaps thaii*). The invention is based, in part, on the discovery that naturally occurring components of hops are useful for the prevention or treatment of a honey bee parasitic mite infestation.

The invention provides a miticidal delivery device for reducing a *Tropilaelaps* spp., (e.g., *Tropilaelaps clareae*, *Tropilaelaps koenigerum*, *Tropilaelaps mercedesae*, and *Tropilaelaps thaii*) infestation in a honeybee, honey bee colony or in a honey bee hive. In one embodiment, the device is a strip comprising hop acids (e.g., alpha, beta acids). In one embodiment, the strip comprises a liquid composition comprising at least about 0.1, 5%, 10%, 15%, 20%, 25%, 30% potassium salts of hop beta acids in solvent (e.g. propylene glycol), and an emulsifier (e.g., polysorbate). In another embodiment, the strip treats or prevents a *Tropilaelaps* spp. infestation, the strip comprising a liquid composition comprising a *Tropilaelaps* spp. killing or repelling effective amount of hop beta acids, an emulsifier, and a solvent. Preferably the strips are moistened with a solution or stable emulsion comprising equal parts beta acid resins dispersed in propylene glycol or another solvent and polysorbate-60 or another emulsifier. The moistened strips are hung within the hive or otherwise placed within the hive where they come in contact with the honey bees, which are infested with parasitic mites. The beta acids kill parasitic mites on contact, and the honey bees disperse the hop beta acids throughout the honey bee hive. Without wishing to be bound by theory, the bees disperse the beta acids throughout the hive during the course of grooming and body-to-body contact. As reported in detail below, hop beta acids were elective in reducing the population of parasitic mites within the hive.

*Apis*

Honey bees are insects that pass through four life stages: the egg, larva, pupa and adult. Adult bees belong to one of three castes: queen, worker, or drone. The queen bee is the only female in the colony that is capable of reproduction and is responsible for all egg production. The worker bees are non-reproductive females who gather honey and care for the queen's progeny, or "brood." The drones are male bees that mate with the queen. The life cycle, from egg to adult bee, takes twenty-one days for worker bees and twenty-four days for drones. The queen bee lays each egg in a single cell of the comb. The egg generally hatches into a larva on the fourth day, which continues its development within the cell. On the ninth day the cell with the developing larva is capped with wax and the larva undergoes pupal metamorphosis. On day twenty-one, a new adult worker bee emerges.

Acarids

Acarids are small parasitic arachnids that act as parasites on a variety of plants and animals, including honey bees. Parasitic mites that prey on honey bees include Asian honey bee mites *Tropilaelaps* spp., (e.g., *Tropilaelaps clareae*, *Tro-*

*pilaelaps koenigerum, Tropilaelaps mercedesae*, and *Tropilaelaps thaii*). *Tropilaelaps* are native to Asia and have spread from their original host the giant honey bee, *Apis dorsata*, to the European honey bee, *A. mellifera*. Mites of the genus *Tropilaelaps* (Acari, Laelapidae) are parasitic mites affecting both developing brood and adult honey bees. *Tropilaelaps* has a higher reproductive rate than *Varroa*. *Tropilaelaps* have a faster development time and a shorter phoretic phase (non-reproductive transport phase, time spent on the adult bees) between reproductive cycles. Consequently, when both types of mite are present in the same colony *Tropilaelaps* populations increase significantly faster than *Varroa*.

Adult *Tropilaelaps* mites enter cells containing larvae where reproduction takes place within sealed brood cells. Typically, the female mite lays eggs on mature bee larvae. Once hatched, the mites feed on the haemolymph (blood) of the pupa (i.e., developing bee). This feeding results in weak and deformed adult bees.

Distinguishing between species of *Tropilaelaps* and *Varroa* is relatively straightforward. *Varroa* mites am larger, crab shaped and wider than they are long, and they move relatively slowly. The body of Tropilaelaps is elongated, and it is a fast running mite, moving rapidly across the brood combs. Unlike the *varroa* mite, *Tropilaelaps* cannot feed on adult bees because its mouthparts are unable to pierce the body wall membrane of the bees.

Tracheal mites are microscopic mites that inhabit the respiratory tubes of bees. *Varroa* mites are ectoparasites that feed on bee hemolymph, and infest wild and domestic honey bee colonies. *Varroa* mite reproduction begins when the adult female mite enters a brood cell shortly before it is capped. Drone brood, which is reared in larger cells than worker brood, is preferentially targeted for mite infestation. The female mite feeds on the larval hemolymph prior to depositing her eggs. The *Varroa* eggs eclose under the sealed cell, and the developing mites feed on the bee pupa. The first egg laid by the female *Varroa* develops into a male. Subsequent eggs develop into females that mate with their brother. The mated female mites along with their mother are released from the capped cell when the bee emerges. The female mites typically attach to adult bees between the abdominal segments or between body regions, where they feed on the bees' hemolymph. Adult bees serve as intermediate hosts and as a means of transport to new sites of infestation.

Desirably, miticides used in acarid control should address the following four needs: i) should disrupt a physiological function required for mite survival; ii) should cause no adult bee mortality: iii) should have no adverse effects on human bee keepers or honey intended for human consumption; and iv) should be capable of delivery into the hive.

Mite Control

Products used to control honey bee parasitic mite infestation reduce, stabilize, or slow the growth of a *Tropilaelaps* spp., (e.g., *Tropilaelaps clareae, Tropilaelaps koenigerum, Tropilaelaps mercedesae*, and *Tropilaelaps thaii*) mite population in a hive or inhibit the growth, survival, reproduction, or other biological function of a *Tropilaelaps* spp., (e.g., *Tropilaelaps clareae, Tropilaelaps koenigerum, Tropilaelaps mercedesae*, and *Tropilaelaps Thaii*) mite. Preferably, the miticide kills the mite. Methods for measuring parasitic mite infestation are known in the art. A number of parameters can be indicative of the level of infestation present in a bee colony: the number of mites present in a sample of bees from an infested hive can be used as one measure of the level of infestation present in the hive; bees reared in a hive having an active infestation are on average smaller than bees reared in a hive without infestation; thus, bee size or weight can be used as another measure of infestation; the amount of honey produced in an infected hive may be less than that produced in a healthy hive; accordingly, honey production could serve as yet another measure of the level of infestation; and finally, severe infestations result in complete loss of colonies. Thus, loss of colonies can be a measure of the level of infestation present in the hive.

In one example, drone brood sampling can be carried out. Capped drone brood are removed from the hive and examined for mites, which are easily visualized against the white pupae. This method measures the percentage of brood that's infected with mites. Natural mite drop onto a sticky board is the most common method used to monitor mites. A sticky or Vaseline-coated board is placed on the floor of the hive, usually with a wire mesh screen on top to keep the bees up off, and the board is left in place for a set period of time. After 1-3 days, the board is removed and the beekeeper counts the number of mites that are on the sticky board. The 24-hour mite drop provides a measure of the level of hive infestation. Alternatively, the board is left in place for 2, 3, or more days and the average number of mites dropped per day is measured.

Powdered sugar sampling is the third common method of monitoring mite populations. In this method, a sample of approximately 300 live nurse bees (½ cup of bees) is scooped up in ajar and shaken gently with powdered sugar for about one minute. The sugar causes the mites to fall off the bees, and the mites are dumped out into a light-coloured dish to be counted. The number of mites per bee—or mites per ½ cup sample provides a measure of the level of infestation.

Alternatively, the sampled bees are killed with a wash of alcohol or soapy water and the sample poured through a double strainer. A coarse mesh catches the bees but allows the mites to pass through, while a second finer screen catches the mites and allows the liquid to flow away. The mites present in the sample are then counted.

In one embodiment, a miticide of the invention reduces the level of infestation in a hive by at least 10%, 25%, 50%, 75% or even by 100%. In another embodiment, a miticide of the invention induces at least 50%, 60%, or 70% mite lethality. Preferably, the miticide induces 75%, 80%, 90%, or even 95% or 100% mite lethality. Screening methods are used to identify concentrations of hop derivatives that will be lethal to a mite (e.g., induce at least 70% mite lethality) while minimizing lethal effects on adult bees.

Alternatively, a miticide of the invention inhibits mite reproduction. Preferably, the miticide reduces mite reproduction by at least 25%, 50%, 75% or 100%. In another approach, the miticide disrupts a biological function required for acarid locomotion; such treatment allows the mite to be trapped, drowned, isolated, or otherwise removed from an area. The invention further provides for mite control in packaged bees and nucleus colonies. Packaged bees and nucleus colonies typically comprise a mated queen and a number of honey bees (e.g., 1, 2, 3, 4, 5 lbs). Packaged bees and nucleus colonies are typically shipped to an end user (e.g., a bee keeper) for use in starting, expanding, or replacing one or more bee hives. Because many bee colonies are infested with honey bee parasitic mites, the shipment of packaged bees and nucleus colonies can spread or increase infestation. Treating packaged bees and nucleus colonies with a composition of the invention can reduce or even eliminate mite infestation in the package or nucleus. In one embodiment, the package or nucleus comprises a strip of the invention. In another embodiment, some portion of the package or container is impregnated with a composition comprising an isolated hop acid or hop acid derivative (e.g., hop beta acids).

Miticide Screening

Commercial products that are currently being used to control mite infestation can be lethal to adult bees when administered at high concentrations, can have adverse effects on human bee keepers, and may contaminate honey intended for human consumption. Conventional miticides include Tau-Fluvalinate (a synthetic-pyrethroid compound used as a selective contact and stomach poison) and Coumaphos (a systemic organic phosphate) used on animals to control lice, ticks and mites. In contrast to conventional miticides, compositions of the invention contain safe natural products derived from hops. Hops have been used for centuries to flavor beer, thus, formulations comprising hop derivatives are generally safe. Miticidal compositions of the invention will not adversely affect human bee keepers or honey intended for human consumption.

Miticides of the invention contain concentrations of hop derivatives that have few or no adverse effects on honey bees during any of their life stages, but are effective in killing or disrupting the biological functioning of a mite. As reported herein, beta acids, a hop derivative, delivered at 4% concentration killed 87% of exposed mites after four hours while causing 0% lethality in adult bees. In one approach, mites are exposed to varying concentrations of hop derivatives to identify those concentrations that kill 50% to 100% of the exposed mite. Adult honey bees are then exposed to concentrations of hop derivatives having miticidal activity to identify those that have a minimal effect on honey bee survival. Preferably, at least 75%, 80%, 85%, 90%, 95%, or 100% of adult bees will survive following exposure to a miticidal composition. In a similar approach, the effect of hop derivatives on mite and honey bee reproduction is assessed. Screening assays are used to determine the concentration of a miticide that reduces the number of eggs laid by the female mite, reduces the number of eggs that hatch, or reduces the number of mites that grow to reproductive maturity; preferably, the reduction is by at least 25%, 50%, 75%, 85%, 95% or 100%.

Hop Derivatives

A hop derivative is a compound that occurs naturally in a hop plant (*Humulus lupulus*) or is chemically derived (either through natural biosynthetic processes (e.g., living organism metabolism (e.g., mammal, plant, bacteria)) or by synthetic processes using human intervention (e.g., chemical synthesis). Compositions of the invention include one or more compounds derived from hops. Of particular interest are the hop acids. Hops contain two major organic acid classes, alpha acids and beta acids. Hop acids are the bitter acid components of hops that are used in beer making. There are three major analogs for alpha acids, humulone, cohumulone, and adhumulone, and three major analogs for beta acids, lupulone, colupulone, and adlupulone. The percentages of the analogs present in the alpha acids and beta acids are variety-dependent. Thus, hop derivatives and hop products typically contain one or a mixture of these analogs. The percentage of analog present is dependent on the hop variety used to produce the derivative or product. Alpha acids and beta acids can be prepared by purification from natural hops and also by chemical synthesis according to traditional methods. Exemplary hop derivatives include beta acids, hexahydrobeta acids, rhoisoalpha acids, isoalpha acids, tetrahydroisoalpha acids, and hexahydroisoalpha acids. Compositions comprising hop derivatives are also available commercially. John I. Haas, Inc. products containing hop derivatives include Redihop®. Isohop®, Tetrahop Gold®, Hexahop Gold®. MgRIAA and MgBeta. The active ingredients in these products are beta acids, rhoisoalpha acids (RIAA), isoalpha acids (IAA), tetrahydroisoalpha acids (THIAA), hexahydroisoalpha acids (HHIAA), magnesium salts of rhoisoalpha acids (MgRIAA) and magnesium salts of beta acids (MgBeta), respectively. For convenience, the identities of these products are also listed in Table 1. These products and/or hop derivatives are typically diluted to a desired concentration for use in the methods of the invention.

Plant extracts are often used for the purification of compounds from plants (e.g., hops). An extract can be prepared by drying and subsequently cutting or grinding the dried material. The term "extract" refers to a concentrated preparation of the essential constituents of a plant, such as hops. Typically, an extract is prepared by drying and powderizing the plant. Optionally, the plant, the dried plant or the powderized plant may be boiled in solution. The extract may be used in liquid form, or it may be mixed with other liquid or solid herbal extracts. Alternatively, the extract may be obtained by further precipitating solid extracts from the liquid form. The extraction process may then be performed with the help of an appropriate choice of solvent, typically ethanol/water mixture, methanol, butanol, iso-butanol, acetone, hexane, petroleum ether or other organic solvents by means of maceration, percolation, repercolation, counter-current extraction, turbo-extraction, or by supercritical carbon-dioxide (temperature/pressure) extraction. The extract may then be further evaporated and thus concentrated to yield by means of air drying, spray drying, vacuum oven drying, fluid-bed drying or freeze-drying, the extract product.

Crude extracts are tested for miticidal activity as described herein. Further fractionation of a positive lead extract having miticidal activity is necessary to isolate chemical constituents responsible for the observed effect. Thus, the goal of the extraction, fractionation, and purification process is the careful characterization and identification of a chemical entity within the crude extract that disrupts a mite biological function. Methods of fractionation and purification of such heterogeneous extracts are known in the art. If desired, compounds shown to be useful as miticides are chemically modified according to methods known in the art.

Numerous methods are available for the chemical synthesis of candidate compounds. Such compounds can be synthesized from readily available starting materials using standard synthetic techniques and methodologies known to those of ordinary skill in the art. Synthetic chemistry transformations and protecting group methodologies (protection and deprotection) useful in synthesizing the compounds identified by the methods described herein are known in the art and include, for example, those such as described in R. Larock, Comprehensive Organic Transformations. VCH Publishers (1989); T. W. Greene and P. G. M. Wuts, Protective Groups in Organic Synthesis, 2nd ed., John Wiley and Sons (1991); L. Fieser and M. Fieser, Fieser and Fieser's Reagents for Organic Synthesis, John Wiley and Sons (1994); L. Paquette, ed., Encyclopedia of Reagents for Organic Synthesis, John Wiley and Sons (1995); and M. Verzele and D. De Keukeleire, Chemistry and Analysis of Hop and Beer Bitter Acids, Elsevier: Amsterdam (1991). Chemically synthesized alpha and beta acids can be separated from a reaction mixture and further purified by a method such as column chromatography, high pressure liquid chromatography, or recrystallization. As can be appreciated by the skilled artisan, further methods of synthesizing the compounds herein will be evident to those of ordinary skill in the art. Additionally, the various synthetic steps may be performed in an alternate sequence or order to give the desired compounds.

The compounds of this invention may contain one or more asymmetric centers and thus occur as racemates and racemic mixtures, single enantiomers, individual diastereomers and diastereomeric mixtures. All such isomeric forms of these compounds are expressly included in the present invention. The compounds of this invention may also be represented in multiple tautomeric forms, in such instances, the invention expressly includes all tautomeric forms of the compounds described herein. All such isomeric forms of such compounds are expressly included in the present invention. All crystal forms of the compounds described herein are expressly included in the present invention. As used herein, the compounds of this invention, including the compounds of formulae described herein, are defined to include derivatives. Derivatives include compounds of the invention that are modified by appending appropriate functionalities to enhance desired properties.

Acceptable salts of the compounds of this invention include those derived from acceptable inorganic and organic acids and bases. Examples of suitable acid salts include acetate, adipate, alginate, aspartate, benzoate, benzenesulfonate, bisulfate, butyrate, citrate, camphorate, camphorsulfonate, digluconate, dodecylsulfate, ethanesulfonate, formate, fumarate, glucoheptanoate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, palmoate, pectinate, persulfate, 3-phenylpropionate, phosphate, picrate, pivalate, propionate, salicylate, succinate, sulfate, tartrate, thiocyanate, tosylate and undecanoate. Other acids, such as oxalic acid, may be employed in the preparation of salts useful as intermediates in obtaining the compounds of the invention and their acceptable acid addition salts. Salts derived from appropriate bases include alkali metal (e.g., sodium), alkaline earth metal (e.g., magnesium), ammonium and N-(alkyl)$_4^+$ salts. This invention also envisions the quaternization of any basic nitrogen-containing groups of the compounds disclosed herein. Water or oil-soluble or dispersible products may be obtained by such quaternization.

In particular, after at least 1 year of storage, the compositions of the invention were found to retain at least about 95%-100% of the hop acids present at the time of application.

Water soluble hop acid alkali metal salts (e.g., sodium, potassium, lithium salts) and water insoluble hop acid alkaline earth metal salts (e.g., calcium, magnesium) are typically present in a diluent or carrier at levels ranging from about 0.1% to about 95%. The methods herein contemplate administration of an effective amount of compound or compound composition to achieve the desired or stated miticidal effect. Preferably, the amount of active ingredient (e.g., hop acid alkali metal salts, hop acid alkaline earth metal salts or combinations thereof) are combined with carrier materials (e.g., maltodextrin, cluster dextrin, corn starch, corn syrup solids, glucose, cyclodextrin, arabic gum, calaginan, inuline, partially hydrogenated soybean oil, cellulose, hydroxymethyl cellulose, hydroxyethyl cellulose, hydroxypropyl cellulose, rosin, hypromellose) to form a powder suitable for delivery. For some applications, miticides of the invention are formulated as liquids using diluents (e.g., sucrose or glucose solutions, water, juices, other aqueous solutions, water miscible solvents (ethanol, cremophor, dimethylsulfoxide (DMSO), dimethylformamide (DMF), isopropanol (IPA) or glycerol, and other solvents)) to form a solution or slurry.

A typical miticidal preparation will contain from about 1% to about 95% hop acid, where the bottom of the range is any integer between 5 and 94 and the top of the range is any integer between 6 and 95, where the hop acids are provided in a carrier (e.g., maltodextrin, cluster dextrin, corn starch, corn syrup solids, glucose, cyclodextrin, arabic gum, calaginan, inuline, rosin, partially hydrogenated soybean oil, cellulose, hydroxymethyl cellulose, hydroxyethyl cellulose, hydroxypropyl cellulose, hypomellose) that is suitable for use in methods of producing a product having miticidal activity. Where non-aqueous miticidal compositions are desired, the miticidal of the invention are preferably formulated with rosin or partially hydrogenated soybean oil. Such compositions may be used for the slow release of the active miticidal composition, for example, in an aqueous slurry. In still other embodiments, miticidal compositions of the invention are dispersed in cellulose powder. In each of the aforementioned embodiments, the hop acid alkali metal (e.g., sodium, potassium, lithium), alkaline earth metal salts (e.g., calcium, magnesium), or other hop acid salts are dispersed or dissolved in water, ethanol, or another diluent together with any one or more of maltodextrin, cluster dextrin, corn starch, corn syrup solids, glucose, cyclodextrin, arabic gum, calaginan, inuline, rosin, partially hydrogenated soybean oil, cellulose, hydroxymethyl cellulose, hydroxyethyl cellulose, hydroxypropyl cellulose, and hypomellose. The composition is then optionally spray dried to facilitate the formation of particles less than 1 mm in size. Preferably, the conditions used for spray drying are adjusted such that the particles are at least about 1 µm, 5 µm, 10 µm, 25 µm, 50 µm, 75 µm, 100 µm, 150 µm, 200 µm, 500 µm, 1 mm, 2 mm, or 5 mm in size. The ratio of hop acids to carrier ranges between about 1:2 and 1:100. Preferred ratios include 1:2, 1:3, 1:4, 1:5, 1:6, 1:7, 1:8, 1:9, 1:10, 1:20, 1:30, 1:50, 1:75, and 1:100. Alternatively, compositions of the invention include at least about 1%, 10%, 20%, 30%, 50%, 60%, 75%, 80%, 90%, or 95% hop acid alkali metal (e.g., sodium, potassium, lithium) or hop acid alkaline earth metal salts (e.g., calcium, magnesium) in a diluent or carrier. Not all of the hop acids need be in the metal form. Anywhere between 5% and 100% of the hop acids present in the composition are in the metal form at any given time, and between 95% and 0% are present as free acids. In various embodiments, a composition of the invention contains hop acids where 90% are present in the metal form and 10% are present in the acid form; 50% are present in the metal form and 50% in the acid form; and 10% are present in the metal form and 90% in the acid form.

In preferred embodiments, the preparation includes between 1 and 95% (e.g., 1, 2, 3, 4, 5, 6, 7, 8, 9, 10, 25%, 75%, 80%, 90%, 95%) hop acids in a carrier or diluent. Alternatively, such preparations contain from about 20% to about 80% hop acids. Compositions containing alpha or beta acids are manufactured by ordinary methods. Hop acids suitable for addition to products can be formulated as ordinary tablets, capsules, solids, liquids, emulsions, slurries, fine granules or powders, which are suitable for administration to products during their preparation, following preparation but prior to storage, or at any time prior to their sale to a vendor or consumer. Lower or higher amounts than those recited above may be required. The compositions delineated herein include the compounds of the formulae delineated herein, as well as additional miticidal agents if present, in amounts effective for inhibiting mite growth or survival. Miticidal compositions of the invention may be used in virtually any application where the inhibition of a mite is desired. For example, compositions of the invention are used to prevent, reduce, inhibit, slow or stabilize the growth, proliferation, or survival of a mite.

Lower or higher doses than those recited herein may be required to effectively kill mites without adversely affecting honey bees. Specific dosage and treatment regimens are determined empirically as described herein. Compositions of the invention are also useful for preventing the establishment of an acarid infestation, for treating an established acarid infestation, and for maintaining the health of a hive previously treated for an acarid infestation.

Formulations

Hop derivatives can be provided to bees or bee hives in a number of convenient formulations. In general, strategies for dispersing a therapeutic or prophylactic agent within the hive rely on i) providing the agent in a food source (e.g., a liquid or solid food): ii) providing the agent in a composition that will induce hygienic behavior designed to remove the composition from the colony (a packet designed to be torn apart by the bees): or iii) providing the agent in a form that the bees will distribute throughout the colony (e.g., a tracking powder provided at an entrance to the hive). Formulations of the invention are used to target mites on the body of adult bees, in the brood cell, or in the hive. Desirably, the composition of the invention is active in the hive for at least forty-one days. This provides for the presence of the miticide for the entirety of the mite life cycle, which typically is completed over the course of twenty-one to thirty days. Where activity is maintained for a shorter period (e.g., seven, fourteen, twenty-one, or thirty days), repeated administration of a composition of the invention may be desired or required. Compositions that are active for longer periods (e.g., two, three, six, nine, or twelve months) are also envisioned. Such compositions may be used for the long-term treatment or prevention of a mite infestation.

Emulsions

Miticides of the invention can also be provided as emulsions or solutions. Emulsion formulations can be found as water in oil (w/o) or oil in water (o/w). Droplet size can vary from the nanometer scale (colloidal dispersion) to several hundred microns. A variety of surfactants and thickeners are usually incorporated in the formulation to modify the size of the droplets, stabilize the emulsion, and modify the release. In one embodiment, hop beta acids (e.g., hop beta acid resins, potassium salts of hop beta acids) are dispersed in solvent (e.g., propylene glycol) to form an emulsion. If desired, the emulsion is stabilized using an emulsifier (e.g., polysorbate 60, lecithin). Emulsifiers are known in the art and described herein. One preferred product for use in treating a honey bee parasitic mite infestation is HopGuard®. Hop Guard is a liquid solution or emulsion that comprises 33.3% potassium hop beta acid resins, 33.3% propylene glycol, and 33.3% polysorbate-60. Preferably, hop beta acids are dispersed in a propylene glycol solvent with polysorbate-60 added as an emulsifier. Biodegradable strips comprising the emulsions are then delivered to the hive. The strips are moistened by contacting them with hop beta acid resins, propylene glycol and polysorbate-60, for example.

Powdered Formulations

Current miticides are introduced into the beehive on plastic non-biodegradable strips that are about 1" wide, 9" long and ¼" thick. Similar means could be used for the delivery of hop derivatives. Other strip compositions include, but are not limited to, membranes, paper, plastic, and polymer strips. In one embodiment, a composition comprising a hop derivative is provided in a powdered formulation. A substrate material is coated with a powdered formulation of hop acids, and the coating is subsequently encased in a layer of a substance that is attractive to bees, such as powdered sugar. This strip is placed inside the beehive where the adult bees chew into the powdered sugar and expose the powdered hop acids. The powdered hop acids get onto the body of the adult bees, thereby contacting mites present on the adult bees and causing the mites to die. Alternatively, the hop acids are consumed by the bees and enter their hemolymph, where they are subsequently consumed by the mites, thereby causing the mites to die.

In another approach, the powdered mixture is delivered to the hive within a semi-permeable pouch that resembles a "teabag". To rid the hive of this foreign object, the bees rip up the pouch, thereby releasing the powder. The powdered hop acids get onto the body of the adult bees and are distributed throughout the hive, thereby killing (or otherwise interfering with mite proliferation or survival) mites present on the bees and inhibiting the mite infestation.

Encapsulated Formulations

In one approach, a hop derivative is provided in an encapsulated formulation (liquid or powder). Preferably, a hop derivative in liquid or powder form is encapsulated in a coating that breaks down slowly inside the beehive. The coating provides for the long-term release of the hop derivative. Preferably, the composition is released over the course of two to six weeks (e.g., two, three, four, five, six weeks). Specific materials suitable for use in capsule materials include, but are not limited to, porous particulates or substrates such as silica, perlite, talc, clay, pyrophillite, diatomaceous earth, gelatin and gels, polymers (e.g., polyurea, polyurethane, polyamide, polyester, etc.), polymeric particles, or cellulose. These include, for example, hollow fibers, hollow tubes or tubing which release a hop derivative or other compound specified above through the walls, capillary tubing which releases the compound out of an opening in the tubing, polymeric blocks of different shapes, e.g., strips, blocks, tablets, discs, which release the compound out of the polymer matrix, membrane systems which hold the compound within an impermeable container and release it through a measured permeable membrane, and combinations of the foregoing. Examples of such dispensing compositions are polymer laminates, polyvinyl chloride pellets, and microcapillaries. Encapsulation methods suitable for use in apiculture are described, for example, by Rieth et al., Journal of Apiculture Research 25(2):78-84 (1986).

Encapsulation processes are typically classified as chemical or mechanical. Examples of chemical processes for encapsulation include, but are not limited to, complex coacervation, polymer-polymer incompatibility, interfacial polymerization in liquid media, in situ polymerization, in-liquid drying, thermal and ionic gelation in liquid media, desolvation in liquid media, starch-based chemistry processes, trapping in cyclodextrins, and formation of liposomes. Examples of mechanical processes for encapsulation include, but are not limited to, spray drying, spray chilling, fluidized bed, electrostatic deposition, centrifugal extrusion, spinning disk or rotational suspension separation, annular-jet encapsulation, polymerization at liquid-gas or solid-gas interface, solvent evaporation, pressure extrusion or spraying into solvent extraction bath.

Microcapsules are also suitable for the long-term release of miticides. Microcapsules are small particles that contain a core material or active ingredient surrounded by a coating or shell. The size of the microcapsule typically varies from 1 to 1000 microns with capsules smaller than 1 micron classified as nanocapsules and capsules larger than 1000 microns as macrocapsules. Core payload usually varies from 0.1 to 98 weight percent. Microcapsules can have a variety of structures (continuous core/shell, multinuclear, or monolithic) and have irregular or geometric shapes.

In another approach, the hop derivative is provided in an oil-based delivery system. The oil-hop derivative mix is deposited on a solid substrate and the substrate containing the hop derivative is placed into the hive where it subsequently contacts and kills the mites. Oil release substrates include vegetable and/or mineral oils. In one embodiment, the substrate also contains a surface active agent that renders the composition readily dispersable in water, such agents include wetting agents, emulsifying agents, dispersing agents, and the like.

Alternatively, miticides of the invention may also be formulated in a solid tablet and comprise (and preferably consist essentially of) an oil, a protein/carbohydrate material (preferably vegetable based), a sweetener and an active ingredient useful in the prevention or treatment of a parasitic infection in a honey bee. Methods for making such compositions are known in the art and are described, for example, in U.S. Patent Publication No. 20060008492. In one embodiment the invention provides a solid tablet and comprises (and preferably consist essentially of) an oil, a protein/carbohydrate material (preferably vegetable based), a sweetener and an active ingredient (e.g., hops α and/or β acid, or combinations or derivatives thereof) useful in the prevention or treatment of a mite infestation. Tablets typically contain about 4-40% (e.g., 5%, 10%, 20%, 30%, 40%) by weight of an oil (e.g., plant oil, such as corn, sunflower, peanut, olive, grape seed, tung, turnip, soybean, cotton seed, walnut, palm, castor, earth almond, hazelnut, avocado, sesame, croton tiglium, cacao, linseed, rape-seed, and canola oils and their hydrogenated derivatives; petroleum derived oils (e.g., parafins and petroleum jelly), and other water immiscible hydrocarbons (e.g., parafins). The tablets further contain from about 5-40% (e.g., 5%, 10%, 20%, 30%, 40%) by weight of a vegetable-based protein/carbohydrate material. The material contains both a carbohydrate portion (e.g., derived from cereal grains, such as wheat, rye, barley, oat, corn, rice, millet, sorghum, birdseed, buckwheat, alfalfa, mielga, corn meal, soybean meal, grain flour, wheat middlings, wheat bran, corn gluten meal, algae meal, dried yeast, beans, rice) and a protein portion. While the relative fraction of each portion making up the material may vary, the material should include at least a portion of carbohydrate and protein.

The tablets also contain between about 10-75% (10, 15, 20, 25, 50, 75%) by weight of a sweetener. As used herein, the term "sweetener" generally refers to both natural and artificial sweeteners. Preferably, the sweetener is a sugar such as glucose, fructose, sucrose, galactose, lactose, and reversed sugar. The sugar is preferably selected from the group consisting of granulated sugar (white sugar), brown sugar, confectioner's sugar, impalpable sugar, icing sugar, and combinations thereof. Alcohols such as glycerin and complex carbohydrates, such as starches may also be used as the "sweetener" ingredient. The sweetener is used primarily as an attractant for the insects, however the sweetener also helps to impart a granular structure to the tablets, especially when the sweetener is a sugar. As previously discussed, this granular structure permits the tablet to crumble over time upon the exertion of sufficient forces.

Optionally, various excipients and binders can be used in order to assist with delivery of the active ingredient or to provide the appropriate structure to the tablet. Preferred excipients and binders include anhydrous lactose, microcrystalline cellulose, corn starch, magnesium estearate, calcium estearate, zinc estearate, sodic carboxymethylcellulose, ethyl cellulose, hydroxypropyl methyl cellulose, and mixtures thereof.

Tablets according to the present invention are manufactured by mixing all of the ingredients together and then compressing the mixture into a tablet of desired shape and size for a particular application. Preferably, the tablet is discoid in shape with a diameter of between about 2-5 inches and a thickness of from about 0.5-2 inches. The pressing may be accomplished by a manual or automatic pressing device. The pressure exerted on the mixture should be sufficient so as to form the tablet into a self-sustaining body.

Methods of delivering an active ingredient to an insect according to the present invention comprise the steps of providing a solid tablet containing the active ingredient as previously described and placing the tablet in a location where the insect may come into direct contact therewith. In treating honeybees that are generally colonized in a manufactured bee hive, the tablet is preferably placed inside the hive.

Over the next several weeks after the tablet is placed into the hive, the bees chew and crumble the tablet exposing the active ingredient to the other bees. The crumbs fall through the brood box away from the honey supers. Preferably, the entire tablet is disintegrated in about 30-45 days.

Miticides of the invention can also be delivered in the form of syrups that are attractive to bees and induce feeding behavior. The syrups for use in the invention preferably comprise sugar and water. Particularly preferred are 50% w/v sucrose solutions. A liquid composition is formed by dispersing hops acids in a sugar syrup comprising 50% sucrose in water. The composition is used as a feed supplement for the bees and can be placed at a suitable location in or near a hive.

Miticides of the invention can also be delivered in packets suitable for inducing hygienic behavior in bees. Such packets are prepared by enclosing a fine powder of hops acids and sugar in a porous material capable of being torn apart by bees. Preferably, the porous material is made of waxed paper or filter paper. Suitable filter papers include those comprising abaca fibers, wood pulp and cellulose rayon fibers. If desired, the paper is coated with polyethylene mixed with copolymers, polypropylene mixed with copolymers or 100% polypropylene.

In other embodiments, miticides are prepared in a dusting composition or as a powder. Dusting compositions are typically prepared by grinding sugar to a fine powder and mixing it into the powder hops acids. Alternatively, the dusting compositions are prepared as described in Example 3 for maltodextrin, where the powder is obtained by spray drying. The skilled artisan adjusts the conditions used in the spray drying process to achieve particles or granules of a size that facilitates delivery to the bees. Desirably, the powder comprises fine particles that coat the bee and all of its body parts (e.g., joints, groove, bristles). The dusting composition can be applied directly to the top of the bee frames, to the combs within the hive, or to the interior surfaces of the hive, or may be applied directly to a bee cluster.

Alternatively, the miticides are prepared in a liquid spray composition that is formed by dispersing hops acids in any suitable liquid. Preferably, the hops acids are dispersed in water. If desired, the spray composition also includes a surfactant that allows the spray to be dispersed efficiently without clogging the spraying apparatus. The composition can be used to spray the hive interior, or the comb, or can be used to spray bee clusters directly.

In another approach, miticides of the invention are delivered in the form of a vapor. Methods for delivering such vapors to a hive are described, for example, in U.S. Patent Publication No. 20020151249.

Miticide Delivery

Devices for delivering pest control agents to bees or to a bee hive are known in the art. Such delivery devices include strips, controlled release strips, tablets, reservoirs, polymer discs, trays, and evaporation devices. If desired, the delivery device is provided as biodegradable form. In one preferred embodiment, the invention provides biogradable strips comprising hop beta acids. Preferably, the strips are moistened with a liquid composition comprising about 16% potassium salts of hop beta acids. In one embodiment, the liquid composition is an emulsion comprising equal parts (i.e., 33.3%) hop beta acid resins, propylene glycol, and polysorbate-60. Moistened strips comprising hop beta acids are hung from the frame of a box hive. In one embodiment, treatment is carried out for 1, 2, 3, 5, 7, 10 days. In another embodiment, treatment is carried out for 2, 3, 4, 5, 6, 8, 10, or 12 weeks. If desired, strips are replaced after they dry out. The treatment is repeated as necessary. Typically two strips/ten frames are used, although higher or lower numbers may be used. In one embodiment, the strips used were about 17" in length and 1¼" wide. In particular embodiments, the strips are biodegradable strips comprising fibers that readily absorb liquid. For example, the strips are made of paper, cardboard, chipboard, or other similar material. The strips are moistened with a liquid hop beta acid composition (e.g., 33.3% hop beta acid resins, 33.3% propylene glycol, 33.3% polysorbate-60) and are shipped or otherwise delivered to the end-use (e.g., hive keeper) in moisture-resistant foil packets. In one embodiment, the strips are about 1-2"(e.g., 1, 1.25, 1.5, 1.75, 2.0") in width by 1-2 feet (e.g., 12, 16, 18, 20, 24") in length.

In another embodiment, the invention provides a corrugated strip comprising a liquid composition comprising hop beta acids for use in treating or preventing a mite infestation in a honey bee hive. In one embodiment, the corrugated strip comprises equal parts beta acid resins, solvent (e.g. propylene glycol), and an emulsifier (e.g., polysorbate). In one embodiment, the beta acid resins comprise at least about 15% potassium salts of beta acids and other extractives. Preferably the corrugated strip is moistened with a solution or stable emulsion comprising equal parts beta acid resins dispersed in propylene glycol or another solvent and polysorbate-60 or another emulsifier for at least about 24-hours or until the desired saturation point is reached. The moistened corrugated strips are packaged for delivery to apiaries. The moistened corrugated strips are hung within the hive where they come in contact with the honey bees, which are infested with parasitic mites. The beta acids kill parasitic mites on contact, and the honey bees disperse the hop beta acids throughout the honey bee hive.

In another embodiment, the invention provides a corrugated strip for treating or preventing a *Tropilaelaps* spp. infestation, the strip comprising a liquid composition comprising a *Tropilaelaps* spp. killing or repelling effective amount of hop beta acids, an emulsifier, and a solvent. In one embodiment, the corrugated strip comprises equal parts beta acid resins, solvent (e.g. propylene glycol), and an emulsifier (e.g., polysorbate). In one embodiment, the beta acid resins comprise at least about 15% potassium salts of beta acids and other extractives. Preferably the corrugated strip is moistened with a solution or stable emulsion comprising equal parts beta acid resins dispersed in propylene glycol or another solvent and polysorbate-60 or another emulsifier for at least about 24-hours or until the desired saturation point is reached. The moistened corrugated strips are packaged for delivery to apiaries. The moistened corrugated strips are hung within the hive where they come in contact with the honey bees, which are infested with parasitic mites. The beta acids kill parasitic mites on contact, and the honey bees disperse the hop beta acids throughout the honey bee hive.

Corrugated sheets useful in the methods of the invention are preferably single-faced sheets (i.e., cardboard having a plain sheet on one side to which a corrugated sheet is affixed). Preferably, corrugated cardboard useful in the methods of the invention are between about 1-2 mm in thickness and comprise preferably about 5, 6, 7, or 8 flutes per inch. In other embodiments, corrugated strips of the invention are about 1 mm, 2 mm, 3 mm, 4 mm, 5 mm, 6 mm, 7 mm, 8 mm, 9 mm, 10 mm, 15 mm, 20 mm, 30 mm, 40 mm in thickness. Single wall and double wall honeycomb cardboard may be used.

In other embodiments, corrugated sheets have the following specifications are useful in the methods of the invention:

| Flute Designation | Flutes per linear foot | Flute thickness (in) | Flutes per linear meter | Flute thickness (mm) |
|---|---|---|---|---|
| A flute | 33 +/− 3 | 3/16 | 108 +/− 10 | 4.8 |
| B flute | 47 +/− 3 | 1/8 | 154 +/− 10 | 3.2 |
| C flute | 39 +/− 3 | 5/32 | 128 +/− 10 | 4.0 |
| E flute | 90 +/− 4 | 1/16 | 295 +/− 13 | 1.6 |
| F flute | 128 +/− 4 | 1/32 | 420 +/− 13 | 0.8 |

Corrugated sheets useful in the methods of the invention may be single or double-faced and are made of paper-based material, engineered wood product comprising wood fibers, plastic, polymer, or any other material known in the art.

For the treatment of packaged bees, strips comprising hop beta acids are hung in the bee packages during shipment.

In particular, devices suitable for delivering a composition of the invention to a parasitic mite, to a honey bee, or to a honey bee hive are described, for example, in U.S. Patent Publication Nos. 20070059333; 20070026765; 20060141904; 200600009122; 20060008492; 20050095954; 20050090560; 20050048093; 20040229542; 20040077291; 20030190860; 20030044443; 20030027490; 20020182977; 20020151249; 20020094756; 20010014346 and 20020151249. Dispensing means and suitable compositions for controlled release are described in U.S. Pat. Nos. 6,843,985; 5,750,129; 4,775,534; 5,849,317; 5,348,511; 6,037,374; 7,137,864; 6,837,770; 6,820,773; 6,702,645; 6,646,014; 6,620,025; 6,595,828; 6,585,557; 6,475,061; 6,468,129; 6,277,371; 6,221,375; 6,204,283; 6,096,350; 6,037,374; 6,010,390; 5,312,622; 5,230,894; 5,227,162; 5,135,758; 5,070,091; 5,069,651; 5,023,359; 4,876,265; 4,867,731; 4,837,216; 4,682,380; and 4,299,816, which are incorporated herein by reference in their entirety.

Kits

The invention provides kits for the treatment or prevention of a *Tropilaelaps* spp., (e.g., *Tropilaelaps clareae*, *Tropilaelaps koenigerum*, *Tropilaelaps mercedesae*, and *Tropilaelaps thaii*) infestation. In one embodiment, the kit includes a composition containing an effective amount of a hop derivative in a form suitable for delivery to a site of infestation (e.g., bee hive). In some embodiments, the kit comprises a container which contains a miticide; such containers can be boxes, ampoules, bottles, vials, tubes, bags, pouches, blister-packs, or other suitable container forms known in the art. Such containers can be made of plastic, glass, laminated paper, metal foil, or other materials suitable for holding miticides.

In particular embodiments, the invention provides a kit that features corrugated strips (e.g., paper, cardboard, chipboard, or other similar material or any other absorbent material known in the art) that are moistened, soaked, or otherwise impregnated with hop beta acids. For example, the strips comprise about 15-20% (e.g., 15, 16, 17, 18, 19, 20%) hop beta acids (e.g., HopGuard®) alone or in combination with other hop derivatives. In one embodiment, the strips comprise a controlled release composition for treating or preventing a parasitic mite infestation, the composition comprising an effective amount of a hop derivative in a suitable form for delivery to a honey bee parasitic mite. Preferably, the strips are in a biodegradable form. In one embodiment, the strips are pre-soaked in a hop acid composition and than packaged in foil, plastic, or similar materials to maintain the strips in a moist condition. If desired the miticide of the invention is provided together with instructions for administering it to a site of infestation. The instructions will generally include information about the use of the composition for the treatment or prevention of an acarid infestation. In other embodiments, the instructions include at least one of the following: description of the miticide; dosage schedule and administration for treatment or prevention of a miticide infestation; precautions; warnings; description of research studies; and/or references. The instructions may be printed directly on the container (when present), or as a label applied to the container, or as a separate sheet, pamphlet, card, or folder supplied in or with the container.

EXAMPLES

Example 1

Hops Beta Acids are Effective at Controlling *Tropilaelaps* Mites as Shown in the Following Tables and in FIG. 1

Beta fraction was used to prepare a 10% aqueous beta acids solution. The term "beta fraction" refers to the oily, waxy, resinous portion of a hop extract obtained when the hop extract is washed with caustic water to remove most of the alpha acids. The beta fraction contains mostly beta acids, resins, oils, and waxes. It is also called beta acid oil. The beta fraction may be used, as is, or washed with caustic water to reduce the alpha acids concentration in the beta fraction so that the ratio of alpha acids to beta acids is 0.05, or below, by HPLC analysis. The temperature of the beta fraction was raised to 60° C. with continuous mixing, and caustic was added in the form of KOH to bring the pH to 10-11. Having first determined the beta acids content in the beta fraction by HPLC analysis, a volume of 60° C. water was added, while mixing, so that the beta acids concentration of the aqueous phase was between 10% and 50%. The pH of the solution was adjusted, if necessary, to pH 10-11 at 60° C. It was necessary to subtract the volume of KOH added for pH adjustment from the calculated volume of water. Also, a temperature range of 55-70° C. was acceptable, although 60° C. was optimal. Mixing was stopped, and the mixture was allowed to sit for at least 45 minutes, during which time the temperature of the solution was maintained at 60° C. The aqueous beta acids phase was then separated from the resinous phase. The aqueous beta acids phase was diluted to a concentration of 10% beta acids as determined by HPLC, while the temperature was maintained at 60° C., and the pH was maintained at 10-11. The aqueous phase was cooled (mixing is optional) to 1-13° C., and allowed to sit for at least 2 hours. The solution was then decanted or filtered.

The 10% beta acids, either prepared as above or directly using the commercially available 10% beta acids, Betastab 10A®, were diluted to produce 1%, 2.5%, 5%, 7.5%, and 10% beta acid solutions by weight. These hop beta acid solutions (1%, 2.5%, 5%, 7.5%, and 10% w/w) and an untreated control were tested for efficacy against *Tropilaelaps* mites. One mL of each test solution was placed on filter paper in a separate petri dish, with each test solution being tested in triplicate. Five *Tropilaelaps* mites were then placed on each of the treated filter papers. *Tropilaelaps* mite mortality was monitored over a 24 hr period.

Table 1, Table 2, and FIG. 1 illustrate the effect of hop beta acid treatment on *Tropilaelaps* mite's mortality, each showing a clear increase in the absolute mortality of the *Tropilaelaps* mites as well as an increase in the rate of mortality of the *Tropilaelaps* mites with increasing hop beta acid concentration. Testing at the 10% w/w hop beta acid top concentration resulted in 100% mortality of the *Tropilaelaps* mite in 3 hr compared to the untreated control, which approached 100% mortality (i.e., 94%) at the 24 hr timepoint. Even at the lowest 1% w/w hop beta acid concentration, 100% mortality of the *Tropilaelaps* mite was effected at the 13 hr timepoint, >twice the mortality rate observed for the untreated control.

Compounds of the invention are prepared in a manner essentially as described above and in the general schemes. The recitation of a listing of chemical groups in any definition of a variable herein includes definitions of that variable as any single group or combination of listed groups. The recitation of an embodiment for a variable herein includes that embodiment as any single embodiment or in combination with any other embodiments or portions thereof. Another embodiment is a compound of any of the formulae herein made by a process delineated herein, including the processes exemplified in the schemes and examples herein. Another aspect of the invention is a compound of any of the formulae herein for use as a miticide as delineated herein. Another aspect of the invention is a compound of any of the formulae herein for use as in the manufacture of a miticide composition as delineated herein.

TABLE 1

Average Number of Dead Tropilaelaps Mites After Treatment With Hop Beta Acids Over 24 Hours
Average Number of dead Tropilaelops mites observed

| Conc. of hop beta acids (% w/w) | Time (hr) | | | | | | |
|---|---|---|---|---|---|---|---|
| | 0 | 1 | 2 | 3 | 4 | 5 | 6 |
| 0% (Control) | 0 | 0 | 0.3 | 0.3 | 0.7 | 0.7 | 0.7 |
| 1% | 0 | 0 | 0 | 0 | 0.7 | 1.7 | 2 |
| 2.50% | 0 | 0 | 0.7 | 1 | 2.7 | 3.7 | 3.7 |
| 5% | 0 | 0 | 1 | 3.3 | 3.7 | 4 | 4 |
| 7.50% | 0 | 0 | 1.7 | 3.7 | 4.7 | 5 | 5 |
| 10% | 0 | 2 | 4.3 | 5 | 5 | 5 | 5 |

| Conc. of hop beta acids (% w/w) | Time (hr) | | | | | | |
|---|---|---|---|---|---|---|---|
| | 7 | 8 | 9 | 13 | 17 | 21 | 24 |
| 0% (Control) | 0.7 | 0.7 | 0.7 | 1.7 | 1.7 | 3.3 | 4.7 |
| 1% | 2.3 | 2.3 | 2.7 | 5 | 5 | 5 | 5 |
| 2.50% | 5 | 5 | 5 | 5 | 5 | 5 | 5 |
| 5% | 5 | 5 | 5 | 5 | 5 | 5 | 5 |
| 7.50% | 5 | 5 | 5 | 5 | 5 | 5 | 5 |
| 10% | 5 | 5 | 5 | 5 | 5 | 5 | 5 |

TABLE 2

Average Percent of Dead Tropilaelaps Mites After Treatment With Hop Beta Acids Over 24 Hours
Average Percent of dead Tropilaelops mites observed

| Conc. of hop beta acids (% w/w) | Time (hr) | | | | | | |
|---|---|---|---|---|---|---|---|
| | 0 | 1 | 2 | 3 | 4 | 5 | 6 |
| 0% (Control) | 0 | 0 | 6 | 6 | 14 | 14 | 14 |
| 1% | 0 | 0 | 0 | 0 | 14 | 34 | 40 |
| 2.50% | 0 | 0 | 14 | 20 | 54 | 74 | 74 |
| 5% | 0 | 0 | 20 | 66 | 74 | 80 | 80 |
| 7.50% | 0 | 0 | 34 | 74 | 94 | 100 | 100 |

TABLE 2-continued

Average Percent of Dead Tropilaelaps Mites After
Treatment With Hop Beta Acids Over 24 Hours
Average Percent of dead Tropilaelops mites observed

| 10% | 0 | 40 | 86 | 100 | 100 | 100 | 100 |

| Conc. of hop | Time (hr) | | | | | | |
|---|---|---|---|---|---|---|---|
| beta acids (% w/w) | 7 | 8 | 9 | 13 | 17 | 21 | 24 |
| 0% (Control) | 14 | 14 | 14 | 34 | 34 | 66 | 94 |
| 1% | 46 | 46 | 54 | 100 | 100 | 100 | 100 |
| 2.50% | 100 | 100 | 100 | 100 | 100 | 100 | 100 |
| 5% | 100 | 100 | 100 | 100 | 100 | 100 | 100 |
| 7.50% | 100 | 100 | 100 | 100 | 100 | 100 | 100 |
| 10% | 100 | 100 | 100 | 100 | 100 | 100 | 100 |

Other Embodiments

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or sub combination) of listed elements. The recitation of an embodiment herein includes that embodiment as any single embodiment or in combination with any other embodiments or portions thereof.

All patents and publications mentioned in this specification are herein incorporated by reference to the same extent as if each independent patent and publication was specifically and individually indicated to be incorporated by reference.

What is claimed is:

1. A strip of plastic, polymer, cardboard, single-faced corrugated sheet, or double-faced corrugated sheet consisting essentially of extracted hop beta acids, polyoxyethylene sorbitan monostearate, and propylene glycol.

2. The strip of claim 1, wherein the single-faced corrugated sheet is a cardboard plain sheet on one side to which a corrugated sheet is affixed.

3. The strip of claim 2, wherein the corrugated sheet is about 2 mm in thickness.

4. The strip of claim 2, wherein the corrugated sheet is 5, 6, 7, or 8 flutes per inch.

* * * * *